United States Patent [19]
Boykin et al.

[11] Patent Number: 6,127,554
[45] Date of Patent: Oct. 3, 2000

[54] **2,4-BIS[(4-AMIDINO)PHENYL]FURANS AS ANTI-*PNEUMOCYSTIS CARINII* AGENTS**

[75] Inventors: David W. Boykin, Atlanta; Richard R. Tidwell, Pittsboro; W. David Wilson, Atlanta; Iris Francesconi, Atlanta, all of Ga.

[73] Assignees: The University of North Carolina at Chapel Hill, Chapel Hill, N.C.; Georgia State University, Atlanta, Ga.

[21] Appl. No.: 09/311,437

[22] Filed: May 14, 1999

Related U.S. Application Data

[62] Division of application No. 09/032,586, Feb. 27, 1998, Pat. No. 6,008,247.
[51] Int. Cl.$^7$ .................................................. C07D 307/38
[52] U.S. Cl. ............................................................. 549/504
[58] Field of Search ............................................. 549/504

[56] References Cited

U.S. PATENT DOCUMENTS

| | | | |
|---|---|---|---|
| 3,359,284 | 12/1967 | Patai et al. | 260/346.1 |
| 3,470,151 | 9/1969 | Doyle et al. | 260/239.1 |
| 5,521,189 | 5/1996 | Boykin et al. | 514/256 |
| 5,602,172 | 2/1997 | Boykin et al. | 514/461 |
| 5,667,975 | 9/1997 | Dykstra et al. | 435/6 |

OTHER PUBLICATIONS

Padmanabhan et al., Bull. Chem. Soc. Jpn., 62(6), pp. 2114–2116, 1989.

*Primary Examiner*—Joseph McKane
*Assistant Examiner*—Taofiq A. Solola
*Attorney, Agent, or Firm*—Myers Bigel Sibley & Sajovec

[57] ABSTRACT

Compounds according to the formula:

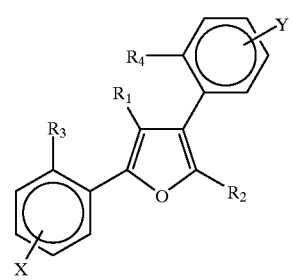

(I)

wherein: $R_1$ and $R_2$ are each independently selected from the group consisting of H, loweralkyl, aryl, alkylaryl, aminoalkyl, aminoaryl, halogen, oxyalkyl, oxyaryl, or oxyarylalkyl; $R_3$ and $R_4$ are each independently selected from the group consisting of H, loweralkyl, oxyalkyl, alkylaryl, aryl, oxyaryl, aminoalkyl, aminoaryl, or halogen; and X and Y are located in the para or meta positions and are each selected from the group consisting of H, loweralkyl, oxyalkyl, and

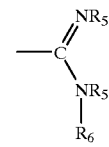

wherein: each $R_5$ is independently selected from the group consisting of H, loweralkyl, alkoxyalkyl, hydroxyalkyl, aminoalkyl, alkylaminoalkyl, cycloalkyl, aryl, or alkylaryl or two $R_5$ groups together represent $C_2$ to $C_{10}$ alkyl, hydroxyalkyl, or alkylene; and $R_6$ is H, hydroxy, loweralkyl, alkoxyalkyl, hydroxyalkyl, aminoalkyl, alkylamino, lkylaminoalkyl, cycloalkyl, hydroxycycloalkyl, alkoxycycloalkyl, aryl, or alkylaryl; or a pharmaceutically acceptable salt thereof, are disclosed. The compounds are useful for treating *Pneumocystis carinii* in a subject in need of such treatment.

8 Claims, No Drawings

2,4-BIS[(4-AMIDINO)PHENYL]FURANS AS ANTI-*PNEUMOCYSTIS CARINII* AGENTS

This application is a divisional of U.S. patent application Ser. No. 09/032,586, filed Feb. 27, 1998, now U.S. Pat. No. 6,008,247 the disclosure of which is incorporated herein by reference.

The present invention was made with Government support under Grant Number HI-33363 from the National Institutes of Health. The Government has certain rights to this invention.

FIELD OF THE INVENTION

The present invention relates to methods of combatting *Pneumocystis carinii* pneumonia with dicationic compounds. Specifically, the present invention relates to methods of combatting *Pneumocystis carinii* pneumonia with bis-aryl furans and novel bis-aryl furans useful therefor.

BACKGROUND OF THE INVENTION

A number of aromatic diamidines have been shown to bind to the minor-groove of DNA, and to exhibit useful antimicrobial activity. Various hypotheses of the mode of antimicrobial action of the aryl amidines have been proposed, however evidence is growing that these compounds function by complex formation with DNA and subsequent selective inhibition of DNA dependent microbial enzymes. Intervention in transcription control has been demonstrated and seems to be a plausible mode of action for structurally diverse minor groove binders. (Das, B. P.; Boykin, D. W., *J. Med. Chem.* 1977, 20, 531–536; Boykin, D. W. et al., *J. Med. Chem.* 1995, 36, 912–916; Kumar, A. et al., *Eur. J. Med. Chem.* 1996, 31, 767–773; Lombardy, R. J. et al., *J. Med. Chem.* 1996, 31, 912–916; Tidwell, R. R. et al., *Antimicrob. Agents Chemother.* 1993, 37, 1713–1716; Tidwell, R. R.; Bell, C. A., Pentamidine and Related Compounds in Treatment of *Pneumocystis carinii* Infection, in *Pneumocystis carinii*, Ed Marcel Decker; New York, 1993, 561–583; Henderson, D.; Hurley, L. H., *Nature Med.* 1995, 1, 525–527; Mote, J. Jr., et al., *J. Mol. Biol.* 1994, 226, 725–737; Boykin, D. W., et al., *J. Med. Chem.* 1998, 41, 124–129).

The antimicrobial and nucleic acid binding properties of amidino- and cyclicamidino-2,5-diarylfurans have been demonstrated. See, e.g., U.S. Pat. No. 5,602,172. The bis (phenylamidinium) compounds have established activity against *Pneumocystis carinii* pneumonia (PCP) in the immunosuppressed rat model. PCP affects a high proportion of patients with suppressed immunsystems such as people with AIDS, and it is a major cause of mortality in these individuals. X-ray crystallographic, molecular modeling and other biophysical studies have demonstrated that these compounds strongly bind to DNA by H-bonding between the furan group and the floor of the minor groove, and by non-bonded interactions to the walls of the AT-rich minor groove.

SUMMARY OF THE INVENTION

As a first aspect, the present invention provides a method of treating *Pneumocystis carinii* pneumonia. The method includes administering to a subject in need of such treatment, an amount effective to treat *Pneumocystis carinii* pneumonia of a compound having the formula:

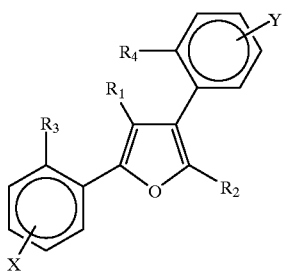

wherein:
$R_1$ and $R_2$ are each independently selected from the group consisting of H, loweralkyl, aryl, alkylaryl, aminoalkyl, aminoaryl, halogen, oxyalkyl, oxyaryl, or oxyarylalkyl;
$R_3$ and $R_4$ are each independently selected from the group consisting of H, loweralkyl, oxyalkyl, alkylaryl, aryl, oxyaryl, aminoalkyl, aminoaryl, or halogen; and
X and Y are located in the para or meta positions and are each selected from the group consisting of H, loweralkyl, oxyalkyl, and

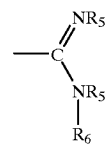

wherein:
each $R_5$ is independently selected from the group consisting of H, loweralkyl, alkoxyalkyl, hydroxyalkyl, aminoalkyl, alkylaminoalkyl, cycloalkyl, aryl, or alkylaryl or two $R_5$ groups together represent $C_2$ to $C_{10}$ alkyl, hydroxyalkyl, or alkylene; and
$R_6$ is H, hydroxy, loweralkyl, alkoxyalkyl, hydroxyalkyl, aminoalkyl, alkylamino, alkylaminoalkyl, cycloalkyl, hydroxycycloalkyl, alkoxycycloalkyl, aryl, or alkylaryl;
or a pharmaceutically acceptable salt thereof.

Compounds according to formula (I) above and the pharmaceutically acceptable salts thereof, pharmaceutical formulations containing the same, and the use of compounds of formula (I) and the pharmaceutically acceptable salts thereof for the preparation of a medicament for treating *Pneumocystis carinii* pneumonia, are also an aspect of the present invention.

The foregoing and other objects and aspects of the present invention are explained in detail in the specification set forth below.

DETAILED DESCRIPTION OF THE INVENTION

The term "loweralkyl," as used herein, refers to $C_1$–$C_6$ linear or branched alkyl, such as methyl, ethyl, propyl, isopropyl, butyl, sec-butyl, iso-butyl, tert-butyl, pentyl, isopentyl, and hexyl. Isoalkyl groups, such as isopropyl, isobutyl, isopentyl, and the like are currently preferred. The term "loweralkoxy" or "oxyalkyl" as used herein, refers to $C_1$–$C_6$ linear or branched alkoxy, such as methoxy, ethoxy, propyloxy, butyloxy, isopropyloxy, and t-butyloxy. Methoxy is currently preferred.

As noted above, the methods of the present invention are useful for treating *Pneumocystis carinii* pneumonia. The methods of the present invention are useful for treating these conditions in that they inhibit the onset, growth, or spread of the condition, cause regression of the condition, cure the condition, or otherwise improve the general well being of a subject inflicted with, or at risk of contracting the condition.

Subjects to be treated by the methods of the present invention are typically human subjects although the methods of the present invention may be useful with any suitable subject known to those skilled in the art. As noted above, the present invention provides pharmaceutical formulations comprising the aforementioned compounds of Formula (I), or pharmaceutically acceptable salts thereof in pharmaceutically acceptable carriers for aerosol, oral, and parenteral administration as discussed in greater detail below. Also, the present invention provides such compounds or salts thereof which have been lyophilized and which may be reconstituted to form pharmaceutically acceptable formulations for administration, as by intravenous or intramuscular injection.

The therapeutically effective dosage of any specific compound, the use of which is in the scope of present invention, will vary somewhat from compound to compound, patient to patient, and will depend upon the condition of the patient and the route of delivery. As a general proposition, a dosage from about 0.1 to about 50 mg/kg will have therapeutic efficacy, with still higher dosages potentially being employed for oral and/or aerosol administration. Toxicity concerns at the higher level may restrict intravenous dosages to a lower level such as up to about 10 mg/kg, all weights being calculated based upon the weight of the active base, including the cases where a salt is employed. Typically a dosage from about 0.5 mg/kg to about 5 mg/kg will be employed for intravenous or intramuscular administration. A dosage from about 10 mg/kg to about 50 mg/kg may be employed for oral administration. The duration of the treatment is usually once per day for a period of two to three weeks or until the condition is essentially controlled. Lower doses given less frequently can be used to prevent or reduce the incidence or recurrence of the infection.

In accordance with the present method, a compound of Formula (I), or a pharmaceutically acceptable salt thereof, may be administered orally or through inhalation as a solid, or may be administered intramuscularly or intravenously as a solution, suspension, or emulsion. Alternatively, the compound or salt may also be administered by inhalation, intravenously or intramuscularly as a liposomal suspension. When administered through inhalation the compound or salt should be in the form of a plurality of solid particles or droplets having a particle size from about 0.5 to about 5 microns, preferably from about 1 to about 2 microns.

Besides providing a method for treating *Pneumocystis carinii* pneumonia, the compounds of Formula (I) also provide a method for prophylaxis against *Pneumocystis carinii* pneumonia in an immunocompromised patient, such as one suffering from AIDS, who has had at least one episode of *Pneumocystis carinii* pneumonia, but who at the time of treatment is not exhibiting signs of pneumonia. As *Pneumocystis carinii* pneumonia is an especially potentially devastating disease for immunocompromised patients it is preferable to avoid the onset of *Pneumocystis carinii* pneumonia, as compared to treating the disease after it has become symptomatic. Accordingly, the present invention provides a method for the prophylaxis against *Pneumocystis carinii* pneumonia comprising administering to the patient a prophylactically effective amount of a compound of Formula (I) or a pharmaceutically acceptable salt thereof. The forms for administration of the compound or salt in accordance with this method may be the same as utilized for the purpose of actually treating a patient suffering from *Pneumocystis carinii* pneumonia.

An additional useful aspect of the present invention is a method for prophylaxis against even an initial episode of *Pneumocystis carinii* pneumonia in an immuno compromised patient who has never experienced an episode of *Pneumocystis carinii* pneumonia. In this respect, a patient who has been diagnosed as being immunocompromised, such as one suffering from AIDS or ARC (AIDS related complex), even before the onset of an initial episode of *Pneumocystis carinii* pneumonia, may avoid or delay suffering from the infection by having administered a prophylactically effective amount of a compound of Formula (I) or a pharmaceutically acceptable salt thereof. The compound or salt may be administered in the same fashion as in the treatment of patients suffering from *Pneumocystis carinii* pneumonia.

The present invention also provides new pharmaceutical compositions suitable for intravenous or intramuscular injection. The pharmaceutical compositions comprise a compound of Formula (I), or a pharmaceutically acceptable salt thereof, in any pharmaceutically acceptable carrier. If a solution is desired, water is the carrier of choice with respect to water-soluble compounds or salts. With respect to the water-insoluble compounds or salts, an organic vehicle, such as glycerol, propylene glycol, polyethylene glycol, or mixtures thereof, may be suitable. In the latter instance, the organic vehicle may contain a substantial amount of water. The solution in either instance may then be sterilized in any suitable manner, preferably by filtration through a 0.22 micron filter. Subsequent to sterilization, the solution may be filled into appropriate receptacles, such as depyrogenated glass vials. Of course, the filling should be done by an aseptic method. Sterilized closures may then be placed on the vials and, if desired, the vial contents may be lyophilized.

In addition to compounds of Formula (I) or their salts, the pharmaceutical compositions may contain other additives, such as pH adjusting additives. In particular, useful pH adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

In yet another aspect of the present invention, there is provided an injectable, stable, sterile composition comprising a compound of Formula (I), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into man. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Other pharmaceutical compositions may be prepared from the compounds of Formula (I), or salts thereof, such as aqueous base emulsions. In such an instance, the composition will contain a sufficient amount of pharmaceutically acceptable emulsifying agent to emulsify the desired amount of the compound of Formula (I) or salt thereof. Particularly useful emulsifying agents include phosphatidyl cholines, and lecithin.

Further, the present invention provides liposomal formulations of the compounds of Formula (I) and salts thereof. The technology for forming liposomal suspensions is well known in the art. When the compound of Formula (I) or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds of Formula (I) or salts thereof, may be lyophilized to produce a lyophilizate which may be reconstituted with a pharmaceutically acceptable carrier, such as water, to regenerate a liposomal suspension.

Pharmaceutical formulations are also provided which are suitable for administration as an aerosol, by inhalation. These formulations comprise a solution or suspension of the desired compound of Formula (I) or a salt thereof or a plurality of solid particles of the compound or salt. The desired formulation may be placed in a small chamber and nebulized. Nebulization may be accomplished by compressed air or by ultrasonic energy to form a plurality of liquid droplets or solid particles comprising the compounds or salts. The liquid droplets or solid particles should have a particle size in the range of about 0.5 to about 5 microns. The solid particles can be obtained by processing the solid compound of Formula (I), or a salt thereof, in any appropriate manner known in the art, such as by micronization. Most preferably, the size of the solid particles or droplets will be from about 1 to about 2 microns. In this respect, commercial nebulizers are available to achieve this purpose.

Preferably, when the pharmaceutical formulation suitable for administration as an aerosol is in the form of a liquid, the formulation will comprise a water-soluble compound of Formula (I) or a salt thereof, in a carrier which comprises water. A surfactant may be present which lowers the surface tension of the formulation sufficiently to result in the formation of droplets within the desired size range when subjected to nebulization.

As indicated, the present invention provides both water-soluble and water-insoluble compounds and salts. As used in the present specification, the term "water-soluble" is meant to define any composition which is soluble in water in an amount of about 50 mg/ml, or greater. Also, as used in the present specification, the term "water-insoluble" is meant to define any composition which has solubility in water of less than about 20 mg/ml. For certain applications, water soluble compounds or salts may be desirable whereas for other applications water-insoluble compounds or salts likewise may be desirable.

Preferred compounds useful for the treatment of *Pneumocystis carinii* pneumonia. The compounds have the structural Formula (I), described above. In particular, compounds useful for the treatment of *Pneumocystis carinii* pneumonia include compounds defined wherein X and Y are located in the para position and are each:

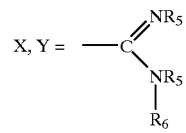

wherein:

(a) $R_1$ is H, $R_2$ is H or loweralkyl, $R_3$ is H, $R_4$ is H, $R_5$ is H, and $R_6$ is isoalkyl, such as isopropyl, isobutyl, isopentyl, and the like;

(b) $R_1$ is H, $R_2$ is H, $R_3$ is H, $R_4$ is H, $R_5$ is H, and $R_6$ is $C_3$–$C_8$ alkoxyalkyl;

(c) $R_1$ is H, $R_2$ is H or loweralkyl, $R_3$ is H, $R_4$ is H, $R_5$ is H, and $R_6$ is alkylhydroxy, such as ethylhydroxy, propylhydroxy, butylhydroxy, pentylhydroxy, and hexylhydroxy;

(d) $R_1$ is H, $R_2$ is H or loweralkyl, $R_3$ is H, $R_4$ is H, $R_5$ is H, and is propoxyethyl;

(e) $R_1$ is H, $R_2$ is H or loweralkyl, $R_3$ is H, $R_4$ is H, $R_5$ is H, and $R_6$ is propoxyisopropyl;

(f) $R_1$ is H, $R_2$ is H or loweralkyl, $R_3$ is H, $R_4$ is H, $R_5$ is H, and $R_6$ is aryl or alkylaryl; and (g) $R_1$ is H, $R_2$ is H or loweralkyl, $R_3$ is H, $R_4$ is H, $R_5$ is H, and $R_6$ is alkylcycloalkyl;

and pharmaceutically acceptable salts thereof.

Examples of compounds exemplary of Formula (I) above include, but are not limited to:
2,4-bis(4-guanylphenyl)furan,
2,4-bis(4-guanylphenyl)-3,5-dimethylfuran,
2,4-bis[2(3,4,5,6-tetrahydropyrimidyl)phenyl]furan,
2,4-bis[4-(2-imidazolinyl)phenyl]furan,
2,4-bis[4-(4,5,6,7-tetrahydro-1H-1,3-diazepin-2-yl)phenyl] furan,
2,4-bis(4-N,N-dimethylcarboxhydrazidephenyl)furan,
2,4-bis[4-(N-isopropylamidino)phenyl]furan,
2,4-bis-{4-[3-(dimethylaminopropyl)amidino] phenyl}furan,
2,4-bis-{4-[N-(3-aminopropyl)amidino]phenyl}furan,
2,4-bis[2-(imidazolinyl)phenyl]-3,5-bis(methoxymethyl) furan,
2,4-bis[4-N-(dimethylaminoethyl)guanyl]phenyl furan,
2,4-bis-{4-[(N-2-hydroxyethyl)guanyl]phenyl}furan,
2,4-bis-[4-N-(cyclopropylguanyl)phenyl]furan,
2,4-bis-[4-N-(N,N-diethylaminopropyl)guanyl]phenyl furan,
2,4-bis-{4-[N-(3-pentylguanyl)]}phenylfuran,
2,4-bis[4-(N-isopropylamidino)phenyl]-5-methylfuran,
and the pharmaceutically acceptable salts thereof.

The synthesis employed for the 2,4-substituted dicationic furans 1–6 used 2,4-bis(4-cyanophenyl)furan as the key intermediate and is outlined in scheme 1. This key compound was obtained through a four step approach. A base catalyzed Aldol condensation between 4-cyanobenzaldehyde and 4-acetylbenzonitrile in methanol gave 1,3-bis(4-cyanophenyl)prop-2-en-1-one. Bromination of the double bond of the chalcone (i) in $CHCl_3$ yielded 1,3-bis(4-cyanophenyl)-2,3-dibromopropan-1-one (ii), which was reacted with 2.5 equivalent of MeONa in MeOH to form 1,3-bis(4-cyanophenyl)-3-methoxyprop-2-en-1-one (iii) (Weygand, C.; Bauer, E.; Hennig, H., Ueber Beziehungen zwischen Polymorphismus und Ethylen-Stereomerie. *B.* 1929, 62, 562–573). The reaction of dimethylsulfonium methylide with the enolether (iii) gave 2,4-disubstituted furan (iv) (Harris, C. M. et al., *J. Org. Chem.* 1974, 39, 72–77).

For the conversion of the 2,4-bis(4-cyanophenyl)furan (iv) into the amidino group a straight forward manner employing the classical Pinner-type method was applied. A suspension of the dinitrile (iv) was stirred in dry EtOH saturated with HCl gas for 3 d to give the imidateester hydrochloride (v), which was allowed to react with the appropriate diamine to form 2,4-bis(4-amidinophenyl)furan.

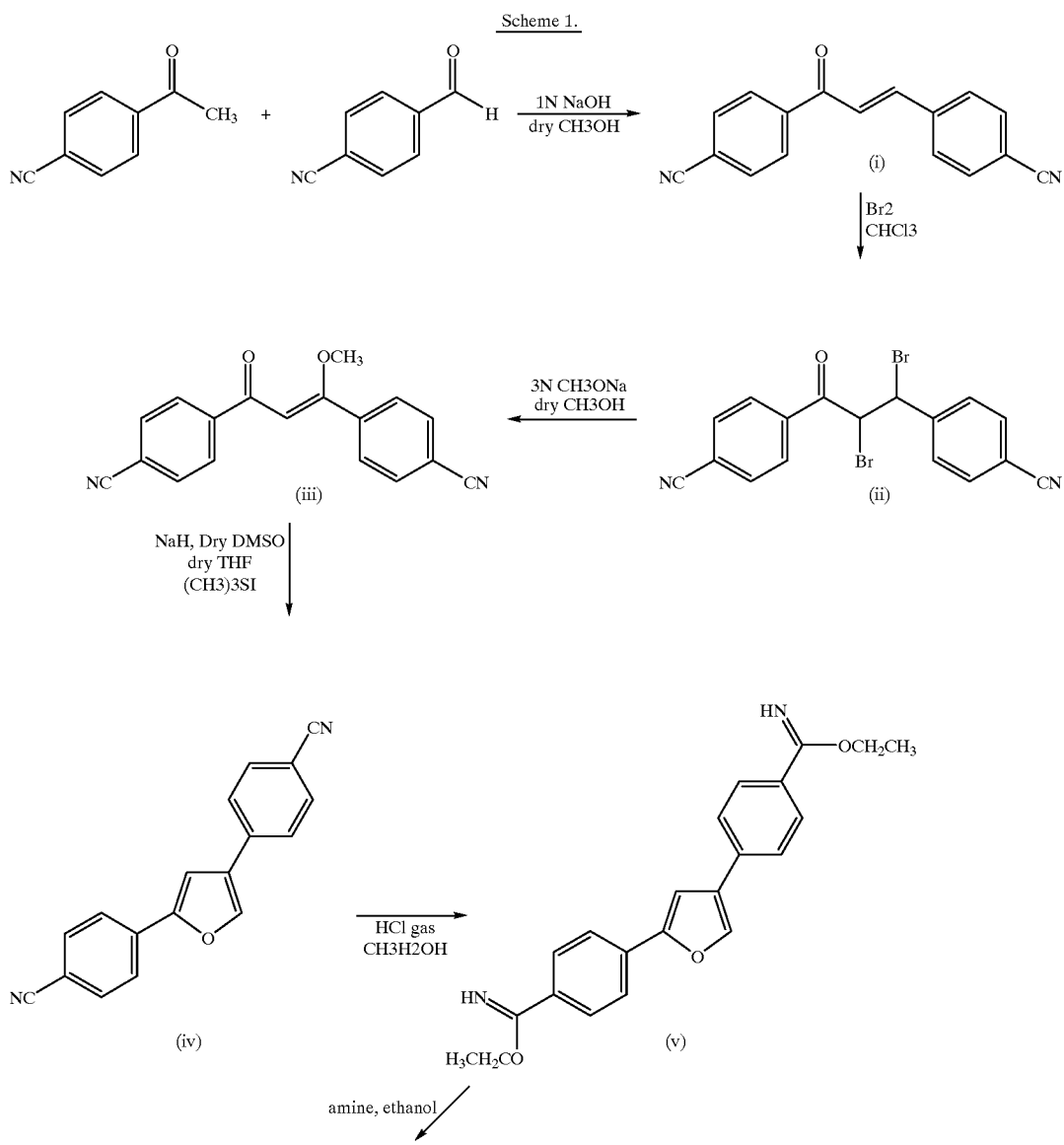

Scheme 1.

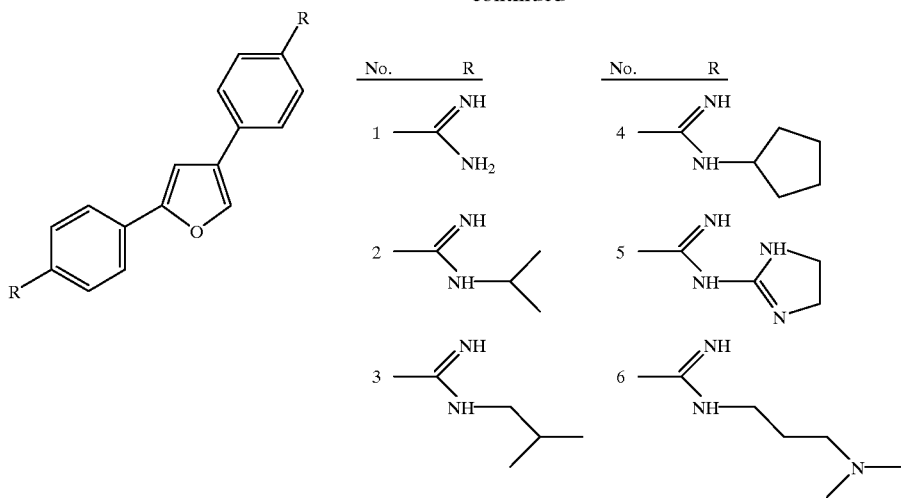

An alternative synthesis is set forth in Scheme 2 for the synthesis of the key intermediate (iv). Step (c) therein represents the cleavage of a non-enolizable ketone group by a Haller-Bauertype reaction. Step (c) may be carried out in a polar or nonpolar aprotic solvent (e.g., dimethylsulfoxide, tetrahydrofuran, dioxane, n-methylpyrrolidone, benzene, in the presence of a strong base (e.g., potassium tert-butoxide, potassium ethoxide, sodium isopropoxide) to form 2,4-bis(4-bromophenyl)furan. Time and temperature are not critical, with room temperature conditions at atmospheric pressure for a time of up to about one hour being typical. Group X is shown in the para position, which is preferred, but may also be in the meta position. The 2,4-bis(4-bromophenyl)furan is converted to 2,4-bis(4-cyanophenyl) furan (iv) by standard procedures (see, e.g., U.S. Pat. No. 5,602,172).

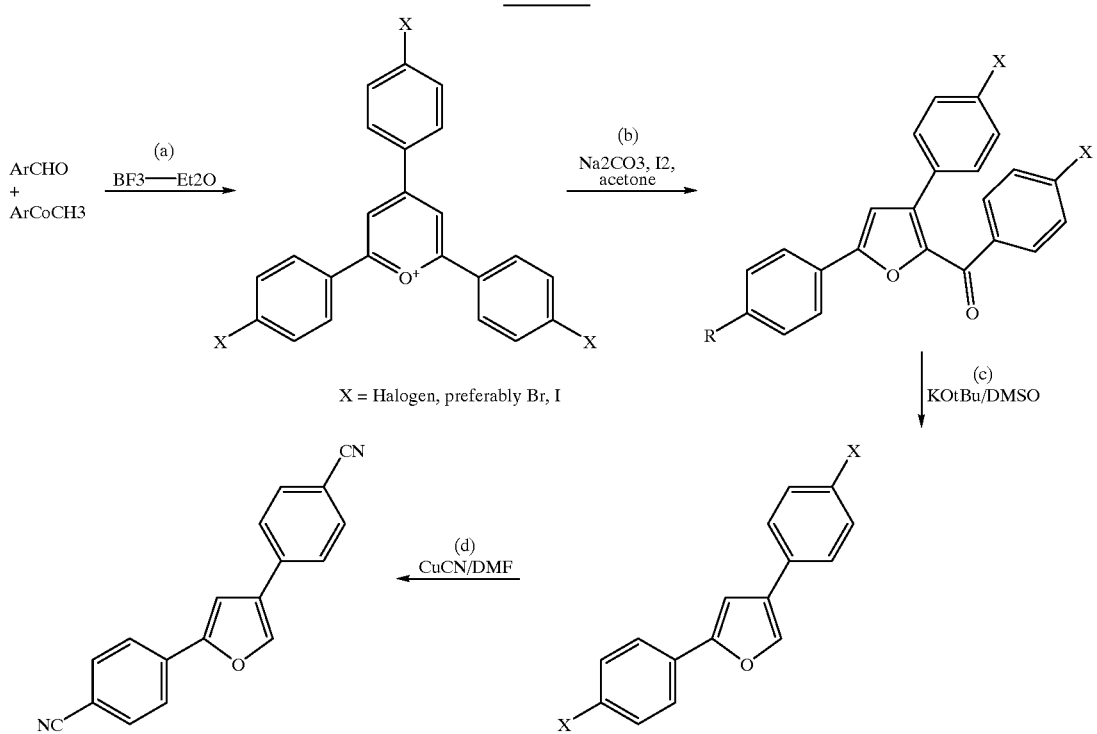

As indicated, the compounds used in the present invention may be present as pharmaceutically acceptable salts. Such salts include the gluconate, lactate, acetate, tartarate, citrate, phosphate, borate, nitrate, sulfate, and hydrochloride salts.

The salts of the present invention may be prepared, in general, by reacting two equivalents of the base compound with the desired acid, in solution. After the reaction is complete, the salts are crystallized from solution by the addition of an appropriate amount of solvent in which the salt is insoluble.

The compounds of the present invention are useful not only in methods for treating *Pneumocystis carinii* pneumonia, but also in methods of inhibiting enzymes such as topoisomerase. The compounds of Formula (I) are particularly useful for inhibiting topoisomerase II. See, S. Doucc-Racy, et al., *Proc. Natl. Acad. Sci. USA* 83:7152 (1986).

In the following examples, all organic extracts were dried over $Na_2SO_4$. All products were dried over $CaSO_4$ under reduced pressure. Melting points were determined in open capillary tubes with a Thomas Hoover and with Mel-temp 3.0 capillary melting point apparatus and are uncorrected. IR spectra were recorded on a Perkin Elmer 2000 FT-IR spectrometer, $^1H$ and $^{13}C$ nuclear magnetic resonance spectra were recorded on a Varian Unity+300 and a Varian VRX 400 instrument. All spectra were in accord with the structures assigned. Elemental analyses were performed on a Perkin Elmer 2400 Series II C, H, N organic elemental analyzer or by Atlantic Microlab, Norcross, Ga. and are within 0.5 of the theoretical values. All chemical and solvents were purchased from Aldrich Chemical Co. or Fisher Scientific. As used herein, "MeONa" means sodium methoxide, "$Et_2O$" means diethyl ether, "THF" means tetrahydrofuran, "DMSO" means dimethylsulfoxide, "MeOH" means methanol, "EtOH" means ethanol, "mp" means melting point, and temperatures are given in degrees centigrade unless otherwise indicated.

EXAMPLE 1

1,3-Bis(4-cyanophenol)-prop-2-en-1-one (I)

10.00 g (76.3 mmol) 4-cyanobenzaldehyde and 11.07 g (76.3 mmol) 4-acetylbenzonitrile were dissolved in 150 mL dry MeOH (distilled from Mg metal), and heated to reflux. Concentrated NaOH was added dropwise until precipitation occurred, and refluxing was continued for another 5 min. The suspension was cooled to room temperature, and the bright yellow solid was filtered, washed with $Et_2O$, and dried. Yield: 12.89 g (65%); mp 113–115° C., bright yellow crystalline solid.

IR (KBr) 2923, 2857, 2228, 1670, 1604, 1466, 1339, 1218, 1036, 992, 816 cm$^{-1}$. $^1H$-NMR (DMSO-$d_6$) δ 8.30 (d, 2H, J=8.1 Hz), 8.10 (d, 2H, J=8.7, Hz), 8.09 (d, 1H, J-15.3 Hz), 8.06 (d, 2H, 7.5 Hz), 7.80 (d, 1H, J=15.6 Hz). $^{13}C$-NMR (DMSO-$d_6$) δ 188.40, 142.77, 140.35, 138.84, 132.71, 132.57, 129.46, 129.09, 124.90, 118.39, 118.00, 115.19, 112.51, Anal. $C_{17}H_{10}N_2O$ (C,H,N).

EXAMPLE 2

1,3-Bis(4-cyanophenyl)-2,3-dibromopropan-1-one (ii)

12.89g (49.9 mmol) of the chalcone i was added to a solution of 2.6 mL $Br_2$ (50.5 mmol) in 150 mL $CHCl_{3abs}$. The suspension was stirred at room temperature for h. The solvent was evaporated under reduced pressure, and the solid was filtered, washed with $Et_2O$, and dried. Yield: 19.78 g (95%); mp 187–189, white crystalline solid.

IR (KBr) 2969, 2923, 2856, 2228, 1691, 1604, 1466, 1406, 1261, 1218, 981, 863, 773, 545 cm$^{-1}$. $^1$HNMR (CDCl$_3$) δ 8.18 (d, 2H, J-8.4 Hz), 7.87 (d, 2H, J=8.8 Hz), 7.75 (d, 2H, J=8.4 Hz), 7.64 (d, 2H, J=8.0 Hz), 6.70 (d, 1H, J=11.2 Hz), 5.62 (d, 1H, J-11.2 Hz), $^{13}$-NMR (CDCl$_3$) δ 189.50, 142.94, 137.40, 133.06, 132.94, 129.47, 129.40, 118.19, 117.85, 117.70, 113.60, 47.55, 46.19. Anal. $C_{17}H_{10}N_2OBr_2$ (C,H,N).

EXAMPLE 3

1,3-Bis(4-cyanophenyl)-3-methoxyprop-2-en-1-one (iii)

A suspension of 15 g (35.9 mmol) dibromochalcone ii in 150 mL dry MeOH (distilled from Mg metal) was heated to reflux. Freshly prepared 3N MeONa (2.49 g Na in 36 mL MeOH) was added dropwise, and stirring was continued for 30 min. The clear orange solution was cooled to room temperature, and poured into 100 mL water. The aqueous suspension was extracted with $CH_2Cl_2$ and the solvent was removed under reduced pressure. The oily orange residue crystallized in part, and was used for the next reaction without further purification.

$^1H$-NMR (CDCl$_3$) δ 7.96 (d, 2H, J=8.8 Hz), 7.75 (d, 2H, J=8.4 Hz), 7.68 (d, 2H, J=8.4 Hz), 7.55 (d, 2H, J=8.4 Hz), 6.28 (s, 1H), 3.99 s, 3H). $^{13}C$-NMR (CDCl$_3$) δ 187.85, 171.27, 142.75, 139.64, 132.61, 131.98, 129.83, 128.68, 118.17, 118.17, 116.06, 114.06, 98.40, 57.26.

EXAMPLE 4

2,4-Bis(4-cyanophenyl)furan (iv)

A suspension of 1.03 g (42.9 mmol) NaH in 15 mL dry DMSO (distilled from $CaH_2$) was stirred at room temperature for 30 min. 30 mL of dry THF (distilled from Na/benzophenone) were added, and the suspension was cooled in a salt/ice bath to 0° C. 8.78 g (43.0 mmol) trimethylsulfonium iodide, dissolved in 15 mL dry DMSO, were added dropwise. The suspension was stirred for another 5 min before a solution of the crude enolether iii, dissolved in 25 mL dry THF, was added. The dark suspension was stirred at ice bath temperature for another 15 min, then ice bath was removed, and stirring was continued for 18 h. The mixture was poured into water, and extracted with CHCl$_3$. The solvent was evaporated, and the oily residue was passed through a silica gel column. Chromatography of the residue with CHCl$_3$-hexane (20+1, 5+1) gave an off-white crystalline solid. Yield: 1.89 g (20% over two steps). mp 229–231° C.

IR (KBr) 2957, 2923, 2854, 2222, 1609, 1464, 1378, 1154, 914, 819 cm$^{-1}$. $^1H$-NMR (CDCl$_3$) δ 7.91 (s, 1H), 7.81 (d, 2H, J=8.8 Hz), 7.72 (d, 2H, J=8.8 Hz), 7.71 (d, 2H, J=8.8 Hz), 7.63 (d, 2H, J=8.8 Hz), 7.12 (s, 1H). $^{13}C$-NMR (CDCl$_3$) δ 153.89, 140.78, 136.53, 134.14, 133.04, 132.95, 127.79, 126.51, 124.47, 118.86, 111.49, 111.31, 106.51. Anal. $C_{18}H_{10}N_2O$ (C,H,N).

EXAMPLE 5

2,4-Bis(4-ethoxyiminoylphenayl)furan Dihydrochloride (v)

0.5 g (1.8 mmol) of the dinitrile iv was suspended in 20 mL of dry ethanol (distilled from Mg metal), and the solution was saturated with HCl gas at ice bath temperature. Stirring was continued at room temperature for another 3 d. The imidate ester hydrochloride was precipitated with 20 mL dry $Et_2O$ (distilled from Na/benzophenone), filtered, and dried under vacuum at room temperature. Yield: 0.80 g (99%).

IR(KBr)2965, 2935, 2867, 1886, 1608, 1465, 1377, 1153, 1020, 932, 751 cm$^{-1}$ $^1H$-NMR (DMSO-$d_6$) δ 8.66 (s, 1H), 8.23 (d, 2H, J=8.4 Hz), 8.21 (d, 2H, J=8.4 Hz), 8.02 (d, 2H, J=8.4 Hz), 7.98 (d, 2H, J=8.4 Hz), 7.96 (s, 1H), 6.17 (q, 4H), 1.52 (t, 6H).

EXAMPLE 6

2,4-Bis[4-{N-(i-propylamidino)phenyl}]furan (2)

A mixture of 1.47 g (3.4 mmol) imidate ester hydrochloride v and 0.75 mL (8.8 mmol) freshly distilled propylamine (distilled from KOH) in 20 mL dry EtOH (distilled from Mg metal) was stirred at room temperature for 3 d. The solvent was removed under reduced pressure, and the residue was suspended in 1N NaOH. After stirring for 30 min the white solid was filtered, washed with water, and dried in vacuo. The white solid was suspended in 30 mL dry EtOH, and the solution was saturated with HCl gas at ice bath temperature. Stirring was continued for 2 h, and the yellow solid was precipitated with dry $Et_2O$, filtered, and dried. Yield: 0.73 g (47%), mp >305° C. decomposition.

$^1$H-NMR(DMSO-$d_6$) δ 8.31 (s, 1H), 7.80–7.67 (m, 8H), 7.54 (s, 1H), 3.81 (m, 2H), 1.14 (d, 12 H, J=4.8 Hz), $^{13}$C-NMR (DMSO-$d_6$) δ 153.61, 139.63, 136.58, 136.14, 132.41, 130.55, 127.36, 126.94, 126.82, 124.81, 122.84, 104.95, 43.44, 22.84. Anal. $C_{24}H_{28}N4O.2HCl.1.5H_2O$ (C,H, N).

EXAMPLE 7

2,4-Bis[4-{N-(cyclopentylamidino)phenyl}]furan (4)

A mixture of 0.53 g (1.2 mmol) imidate ester hydrochloride v and 0.27 mL (2.7 mmol) freshly distilled cyclopentylamine (distilled from KOH) in 20 mL dry EtOH (distilled from Mg metal) was stirred at room temperature for 24 h. 20 mL 1N NaOH were added, and stirring was continued for 30 min. The solid was filtered, washed with $H_2O$, and dried under reduced pressure. The free amidine base was suspended in 20 mL dry EtOH, and the solution was saturated with HCl gas at ice bath temperature. After stirring for 5 h the yellow solid was precipitated with dry $Et_2O$ (distilled from Na/benzophenone), filtered, and dried. Yield: 0.43 g (69%), mp >302° C. decomposition.

$^1$H-NMR (DMSO-$d_6$) δ 8.25 (s, 1H), 7.87 (d, 2H, J=8.0 Hz), 7.77 (d, 2H, J=8.0 Hz), 7.67 (t, 4H), 7.52 (s, 1H), 4.00 (m, 2H), 2.00 (m, 8H). $^{13}$C-NMR (DMSO-$d_6$) δ 163.62, 154.38, 142.63, 137.45, 135.17, 129.90, 129.84, 128.74, 128.43, 128.29, 127.13, 125.13, 107.70, 55.67, 32.46, 24.61. Anal. $C_{28}H_{34}H_4O.2HCl.5/4H_2O$ (C,H,N).

EXAMPLE 8

2,4-Bis[4,5-dihydro-1H-imidazol-2-yl)phenyl]furan Dihydrochloride (5)

0.14 mL (2.1 mmol) dried and freshly distilled 1,2-diaminoethane (distilled from KOH) was added to a suspension of 0.41 g (0.9 mmol) imidate ester hydrochloride 5 in 20 mL dry EtOH (distilled from Mg metal), and the solution was refluxed for another 16 h. The solvent was removed under reduced pressure, and the residue was suspended in 20 mL 1 N KOH, and stirred for 30 min. The solid was filtered, washed with $H_2O$, and dried in vacuo. The free imidazoline base was suspended in 20 mL dry EtOH, and the solution was saturated with HCl gas at ice bath temperature. After stirring for 2 h the imidazoline salt was precipitated with dry $Et_2O$ (distilled from Na/benzophenone), filtered, and dried. Yield: 0.022 g (49%) mp >300° C.

$^1$H-NMR (DMSO-$d_6$) δ 8.21 (s, 1H), 7.90–7.78 (m, 8H), 7.48 (s, 1H), 3.96 (t, 8H). $^{13}$C-NMR (DMSO-$d_6$) δ 167.05, 166.93, 154.74, 143.67, 139.13, 136.65, 130.47, 128.68, 127.86, 125.85, 122.31, 122.05, 108.60, 45.97. Anal. $C_{22}H_2ON_4O.2H_2O$ (C,H,N).

TABLE 1

ELEMENTAL ANALYSIS DATA

| Com- pound # | | Calculated Values | | | Found Values | | |
|---|---|---|---|---|---|---|---|
| | | % C | % H | % N | % C | % H | % N |
| i | $C_{17}H_{10}N_2O$ | 79.06 | 3.90 | 10.85 | 78.89 | 3.83 | 10.96 |
| ii | $C_{17}H_{10}N_2OBr_2$ | 48.84 | 2.41 | 6.70 | 48.55 | 2.22 | 6.26 |
| iv | $C_{18}H_1N_2O$ | 79.99 | 10.36 | 3.73 | 79.90 | 10.34 | 3.74 |
| 5 | $C_{24}H_{28}N_4O.2HCl$ $1.5H_2O$ | 59.56 | 6.77 | 11.58 | 59.20 | 6.37 | 11.42 |
| 2 | $C_{28}H_{34}N_4O.2HCl$ $5/4H_2O$ | 64.18 | 7.02 | 10.69 | 63.80 | 6.51 | 10.47 |
| 4 | $C_{22}H_{20}ON_4O.2HCl$ $2H_2O$ | 56.78 | 5.63 | 12.04 | 56.85 | 5.47 | 11.77 |

EXAMPLE 9

Biological Activity

Table 2 contains thermal melting results from evaluation of the interaction of compounds 3, 5 and 7 with the DNA duplex polymer poly(dA-dT). In order to rank the relative binding affinities for interactions with DNA, the duplex oligomer d(CGCGAATTCGCG)$_2$ ($A_2T_2$) was employed. The melting temperature range for this oligomer allows measurement of ΔTm values for these compounds, even though they exhibit strong binding affinities. The increase in melting temperature on complex formation with the furan dications are related to the binding affinities of these molecules with nucleic acid. This enhanced DNA affinity of the N-alkyl substituted amidines is though to the in large part due to additional non-bonded interactions between the alkyl groups and the walls of the minor groove.

Table 2 also shows the results from the in vivo evaluation of the furan dications on intravenous administration against P. carinii in the immunosuppressed rat model. Data obtained with pentamidine, a compound currently used clinically for treatment of PCP, are included for comparison. All of the reported compounds are more active than pentamidine, with no overt toxicity at the screening dose, in the immunosuppressed rat model for Pneumocystis carinii pneumonia.

TABLE 2

Nucleic acid binding results and in vivo activity of 2,4-dicationic furans against Pneumocystis carinii.

| Compound # | ΔTm[a] (DNA) | ΔTM[b] (oligomer) | Dosage[c] (umol/kg/d) | Cysts/g lung[c] (% of control) | Toxicity[c] |
|---|---|---|---|---|---|
| saline | | | | 100.0 | |
| pentamidine | | | 22.0 | 1.46 | ++ |
| 1 | 19.0 | 9.1 | 10.0 | 0.44 | 0 |
| 2 | 17.6 | 10.9 | 10.0 | 0.03 | 0 |
| | | | 5.0 | 0.0003 | 0 |
| | | | 1.0 | 0.84 | 0 |
| | | | 0.25 | 38.20 | 0 |
| 3 | 20.4 | 9.3 | | | |
| 4 | 20.4 | 13.6 | 10.0 | 0.06 | 0 |
| | | | 1.0 | 3.21 | |
| 5 | 16.8 | 7.2 | | | |

[a])Increase in thermal melting of polyA_polyT, see Boykin, D. W., et al., J. Med. Chem. 1998, 41, 124–129.
[b])Increase in thermal melting of the oligomer d(GCGCAATTGCGC)2, see Boykin, supra.
[c])Evaluation of iv dosage of the furon dicatons against P. carinii in rats as descibed in Boykin, supra.

EXAMPLES 10–13

Alternate Synthesis Scheme

The following examples illustrate an alternate synthetic route to compounds of the present invention.

EXAMPLE 10

2,4,6-Tris(4-bromophenyl)pyryllium tetrafluoroborate 4.65 g (25.1 mmol) 4-bromobenzaldehyde and 10 g (50.2 mmol) 4' bromoacetophenone were mixed thoroughly and dissolved in 5 mL anhydrous benzene. Under nitrogen atmosphere 7.13 mL (59.0 mmol) $BF_3.Et_2O$ were added and the clear yellow solution was heated to reflux for 2 h. After cooling to room temperature 5 mL acetone were added and the mixture was poured on 300 mL $Et_2O$. The bright yellow precipitation was filtered and dried over $CaSO_4$ in vacuo. Without further identification or purification the solid product was used for the next reaction step. Yield: 4.82 g (30%).

EXAMPLE 11

2-(4-Bromobenzoyl)-3.5-bis(4-bromophenyl)furan 4.82 g (7.6 mmol) of 2,4,6-tris(4-bromophenyl)pyryllium tetrafluoroborate were suspended in 40 mL acetone and 4.9 mL 2.5 M $Na_2CO_3$ solution was added. The suspension was stirred at room temperature for 2 h. 3.09 g (12.2 mmol) iodine were added and stirring was continued for 16 h. The dark brown mixture was pored into a solution of 9.62 g (60.8 mmol) $Na_2S_2O_3$ in 200 mL $H_2O$. The aqueous phase was extracted with $CHCl_3$ and the organic phase was washed with water, dried over $NA_2SO_4$ and reduced under vacuum. The light yellow product was recrystallized from MeOH/$Et_2O$. Yield: 3.01 g (70%) mp 186–188° C.

IR (KBr) 2956, 2923, 2854, 1637, 1598, 1583, 1526, 1483, 1471, 1413, 1397, 1374, 1308, 1288, 1216, 1179, 1074, 1010, 998, 934, 895, 816, 807, 750, 708, 649 cm$^{-1}$. 1H-NMR (CDCl$_3$) δ 7.84 (d, 2H, J=8.4 Hz), 7.63 (d, 6H, J=9.2 Hz), 7.55 (d, 2H, J=9.2 Hz), 7.53 (d, 2H, J=9.2 Hz), 6.97 (s, 1H). $^{13}$C-NMR(CDCl$_3$) δ 182.1, 155.4,146.1, 137.0, 136.8, 132.6, 131.8, 131.7, 131.4, 131.0, 130.9, 128.1, 127.8, 126.6, 124.0, 123.3, 110.2. Anal. Calcd for $C_{23}H_{13}O_2Br_3$: C, 49.2; H, 2.3. Found: C, 48.5; H, 2.3.

EXAMPLE 12

2,4-Bis(4-bromophenyl)furan 0.27 mL of water was added to a solution of 5.70 g (50.8 mmol) Bu$^t$OK in 50 mL anhydrous DMSO. 2.85 g (5.1 mmol) 2-(4-bromobenzoyl)-3,5-bis(4-bromophenyl)furan was added and stirring was continued for 1 h. The dark mixture was slowly poured into 300 mL ice water and the aqueous phase was extracted with CHCl$_3$. The organic phase was washed with water, dried over Na$_2$SO$_4$, filtered and reduced under vacuum. The crude product was purified by column chromatography on silica gel. Yield: 1.27 g (66%); mp 154–156° C.

IR (KBr) 2956, 2927, 2855, 1464, 1413, 1378, 1105, 1079, 913, 831, 802, 764, 621 cm$^{-1}$. $^1$H-NMR (CDCL$_3$), δ 7.72 (s, 1H), 7.55 (d, 2H, J=8.8 Hz), 7.51 (d, 2H, J=8.8 Hz), 7.50 (d, 2H, J=8.4 Hz), 7.36 (d, 2H, J=8.4 Hz), 6.89 (s, 1H). $^{13}$C-NMR (CDCl$_3$) δ 154.1, 138.3, 132.0, 131.9, 131.1, 129.4, 127.6, 125.4, 121.6, 121.0, 104.3. Anal. Calcd for $C_{16}H_{10}OBr_4$: C, 50.8; H, 2.7. Found: C, 50.4; H, 2.5.

EXAMPLE 13

2,4-Bis(4-cyanophenyl)furan

To 1.35 g (15.1 mmol) Cu(I)CN is added 30 mL dry DMF (distilled over CAH$_2$), and the suspension is slightly heated until a clear green solution occurs. 1.61 g (4.3 mmol)2,4-Bis(4-bromophenyl)furan is added, and the mixture is heated to reflux for 48 h. The hot suspension is poured on 500 mL water, and the dark green solid is filtered and dried over CaSO$_4$ under reduced pressure. The crude product is extracted with acetone in a Soxlette extraction apparatus, and the solvent is removed in vacuo to give an off-white crystalline product. Yield: 0.56 g (49%) mp 229–231. The compound is identical with iv in Example 4.

EXAMPLE 14

2,4-Bis[4-{(amidino)pnehyl}]furan (1)

A suspension of 0.80 g (1.8 mmol) imidate ester hydrochloride in 20 mL dry EtOH (distilled from Mg metal) was cooled to 0° C. in an ice bath, and saturated with dry NH$_3$ gas. The ice bath was removed, and stirring was continued for 72 hours. After addition of 20 mL 1N NaOH the white suspension was stirred for another hour, the solid was filtered, washed with water and dried over CaSO$_4$ under reduced pressure. For purification the crude product was heated in dry EtOH for 30 minutes, again filtered and dried over CaSO$_4$. A suspension of the free base in 20 mL dry EtOH was saturated with dry HCl gas at 0° C., and stirring was continued for 2 hours at room temperature. The yellow solid was precipitated with dry Et$_2$O, filtered and dried. mp>346° dec. yield 0.42 g (96%).

$^1$H-NMR (DMS)-d$_6$: D$_2$O 1:1) δ 8.33 (s, 1H), 7.92 (d, 2H, J=8.4 Hz), 7.84–7.78 (m, 6H), 7.60 (s, 1H). $^{13}$C-NMR (DMSO-D$_6$:D$_2$O 1:1) δ 166.36, 166.26, 154.09, 142.91, 137.96, 135.56, 129.75, 129.67, 128.06, 127.38, 127.12, 127.06, 125.08, 107.91. Anal $C_{18}H_{16}N_4O.2HCLxH_2O$ (C,H, N)

EXAMPLE 15

2-4-Bis[4-{N-(i-butlyamidino)phenyl}]furan (3)

A mixture of 0.64 g (1.5 mmol) imidate ester hydrochloride (v) and 0.32 mL (3.2 mmol) i-butylamine in 10 mL dry EtOH (distilled from Mg metal) was stirred for 2 days at room temperature. 10 mL 1N NaOH was added to the light yellow suspension and stirring was continued for another 1.5 hours. The mixture was poured into 150 mL H$_2$O and the off-white precipitation was filtered, washed with H$_2$O and dried over CaSO$_4$ under vacuum. The crude product is recrystallized from EtOH/Et$_2$O. The free base was dissolved in 10 mL dry EtOH, and the solution was saturated with HCl gas at ice bath temperature. Stirring was continued at room temperature for 2 hours, and the light yellow solid was precipitated with dry Et$_2$O, filtered, and dried. Yield: 0.36g (50%) mp 278° C. dec.

$^1$H-NMR (DMSO-D$_6$: D$_2$O 1:1) δ 8.47 (s, 1H), 7.95 (d, 2H, J=8.0 Hz), 7.89 (d, 2 H, J=8.0 Hz), 7.81–7.74 (m, 5H), 3.23 (t, 4H), 2.00 (m, 2H), 0.96 (m 12H). $^{13}$C-NMR (DMSO-d$_6$: D$_2$O 1:1) δ 163.3, 163.2, 153.4, 142.3, 136.7, 134.4, 129.3, 129.2, 128.0, 127.7, 127.5, 126.2, 124.2, 107.3, 49.9, 27.3, 20.2. Anal. Calcd for $C_{26}H_{32}N_4O.2HCl.1H_2O$: C, 61.5; H, 7.2; N, 11.0. Found: C, 61.8, H, 7.0; N, 10.9.

EXAMPLE 16

2-,4-Bis [4-{N,N-dimethylamino)propylamidino)phenyl}]furan (6)

A mixture of 0.71 g (1.6 mmol) imidate ester hydrochloride (v) and 0.42 mL (3.3 mmol) N,N-dimethyl-1,3- diaminopropan in 20 mL dry EtOH (distilled over Mg metal) was stirred at room temperature for 4d. The solvent was removed under reduced pressure, and the oily residue was suspended in a mixture of 20 mL 1N NaOH and 1 mL EtOH. After stirring for 1 hour the white solid was filtered, washed with water and dried over $CaSO_4$ in vacuo. The crude product was recrystallized from $CHCl_3$/hexane to give a white solid. The free base was suspended in 20 mL dry EtOH, and the solution was saturated with dry HCl gas at ice bath temperature. Stirring was continued for 2 h, and the solid was precipitated with dry $Et_2O$, filtered, and dried. Yield: 0.56 g (56%); mp 298° C.

$^1$H-NMR ($CDCl_3$) δ 7.81 (s, 1H), 7.74 (d, 2H, J=8.4 Hz), 7.65 (t, 4H), 7.56 (d, 2H, J=8.4 Hz), 7.03 (s, 1H), 3.45 (t, 4H), 2.27 (s, 12H), 1.85 (m, 4H). $^1$H-NMR ($CDCl_3$) δ 162.31, 162.24, 152.79, 141.85, 136.17, 133.83, 128.88, 128.71, 127.31, 126.94, 126.83, 125.36, 123.26, 106.87, 53.82, 41.91, 22.31. Anal. $C_{28}H_{38}N_6O.4HCl.1H_2O$ (C, H, N).

The foregoing is illustrative of the present invention, and is not to be construed as limiting thereof. The invention is defined by the following claims, with equivalents of the claims to be included therein.

We claim:

1. A method of making a compound of formula (c):

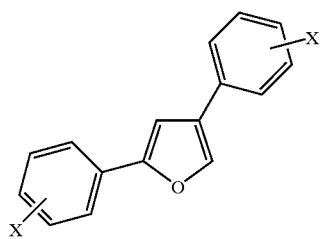

(c)

wherein X is halogen; comprising:
reacting a compound of formula (d):

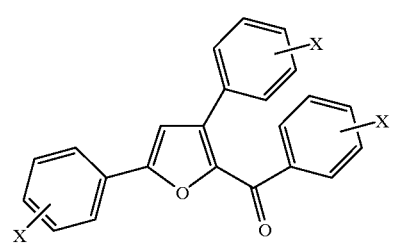

(d)

in the presence of a base to form the compound of formula (c).

2. A method according to claim 1, wherein X is selected from the group consisting of Br and I.

3. A method according to claim 1, wherein X is in the para position.

4. A method according to claim 1, wherein X is in the meta position.

5. A method according to claim 1, wherein said reacting step is carried out in a polar or nonpolar aprotic solvent.

6. A method according to claim 1, wherein said reacting step is carried out in a solvent selected from the group consisting of dimethylsulfoxide, tetrahydrofuran, dioxane, n-methylpyrrolidone, and benzene.

7. A method according to claim 1, wherein said base is selected from the group consisting of potassium tert-butoxide, potassium ethoxide, and sodium isopropoxide.

8. A method according to claim 1, wherein:
X is selected from the group consisting of Br and I;
X is in the para position;
said base is selected from the group consisting of potassium tert-butoxide, potassium ethoxide, and sodium isopropoxide; and
said reacting step is carried out in a solvent selected from the group consisting of dimethylsulfoxide, tetrahydrofuran, dioxane, n-methylpyrrolidone, and benzene.

* * * * *